United States Patent [19]

Dittrich et al.

[11] 4,017,638
[45] Apr. 12, 1977

[54] ISO-(THIO)-UREA DERIVATIVES

[75] Inventors: Volker Dittrich, Zeiningen; Werner Töpfl, Dornach; Odd Kristiansen, Möhlin, all of Switzerland

[73] Assignee: Ciba-Geigy Corporation, Ardsley, N.Y.

[22] Filed: Mar. 3, 1976

[21] Appl. No.: 663,413

[30] Foreign Application Priority Data

Mar. 5, 1975 Switzerland ............ 2761/75
Feb. 4, 1976 Switzerland ............ 1359/76

[52] U.S. Cl. ............... 424/326; 260/556 A; 260/556 AR; 260/556 B; 260/564 E; 424/321
[51] Int. Cl.² .................. C07C 123/00
[58] Field of Search .... 260/564 E, 556 A, 556 AR, 260/556 B; 424/326, 321

[56] References Cited

UNITED STATES PATENTS 3,625,992 12/1971 Duerr et al. ............ 424/246
3,852,463 12/1974 Widdig et al. ............ 424/263

Primary Examiner—Gerald A. Schwartz
Attorney, Agent, or Firm—Harry Falber

[57] ABSTRACT

Iso-(thio)-urea derivatives of the formula

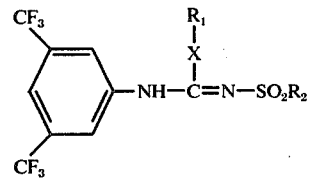

wherein
$R_1$ and $R_2$ each represent $C_1-C_5$-alkyl or phenyl or benzyl mono-, di- or trisubstituted by halogen, trifluoromethyl, nitro and/or methyl, and
X represents oxygen or sulphur, processes for their production and their use in pest control.

6 Claims, No Drawings

ISO-(THIO)-UREA DERIVATIVES

The present invention relates to iso-(thio)-urea derivatives, to processes for their production, and to their use in pest control.

The iso-(thio)-urea derivatives have the formula

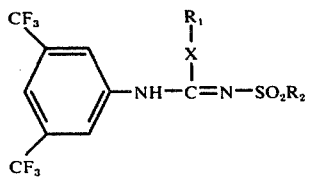 (I)

wherein $R_1$ and $R_2$ each represent $C_1$–$C_5$-alkyl or phenyl or benzyl mono-, di- or trisubstituted by halogen, trifluoromethyl, nitro and/or methyl, and X represents oxygen or sulphur.

By halogen is meant fluorine, chlorine, bromine or iodine, particularly however chlorine.

Alkyl groups denoted by $R_1$ and $R_2$ can be branched-chain or straight-chain. Examples of such groups are: methyl, ethyl, propyl, isopropyl, n-, i-, sec.-, tert.-butyl, n-pentyl and isomers thereof.

Compounds of the formula I which are of special importance on account of their action are those wherein $R_1$ represents methyl, $R_2$ represents phenyl mono-, di- or trisubstituted by chlorine, and X represents sulphur.

The compounds of the formula I are obtained by the following known method comprising reacting, e.g., the compound of the formula

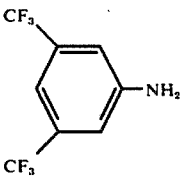 (II)

in the presence of an acid-binding agent with a compound of the formula

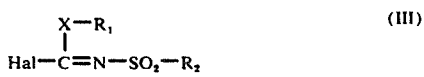 (III)

wherein $R_1$, $R_2$ and X have the meanings given for the formula I, and Hal stands for a halogen atom, especially for a chlorine atom. Suitable acid-binding agents are, e.g., tertiary amines such as trialkylamines, also hydroxides, oxides, carbonates and bicarbonates of alkali metals and alkaline-earth metals, as well as alkali metal alcoholates such as potassium-t.butylate and sodium methylate. The process is performed at a reaction temperature of between $-10°$ and $100°$ C, particularly between $20°$ and $80°$ C, under normal or elevated pressure, and preferably in a solvent or diluent inert to the reactants.

Suitable solvents or diluents are, for example, ethers and ethereal compounds such as diethyl ether, dipropyl ether, dioxane, dimethoxyethane or tetrahydrofuran; amides such as N,N-dialkylated carboxylic acid amides; aliphatic, aromatic as well as halogenated hydrocarbons, especially benzene, toluene, xylenes, chloroform or chlorobenzene; nitriles such as acetonitriles; and ketones such as acetone or methyl ethyl ketone. The starting materials of the formulae II and III are known and can be produced by methods known per se (see Chem.Ber. 99, 2885 (1966); Angew.Chemie 77, 549 (1965 or Chem.Ber. 99, 1252 (1966).

The compounds of the formula I exist as follows in two possible isomeric forms:

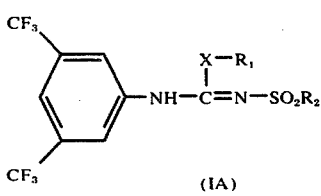 (IA)

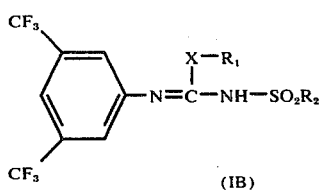 (IB)

Mixtures of these two forms might be obtained by the production method described above. Furthermore, the two forms exhibit a syn/anti isomerism. As is shown by NMR spectra, however, it is to be assumed that only homogeneous compounds of the structure IA are obtained by the production method described.

The compounds of the formula I are suitable for the control of various animal and plant pests.

These compounds exhibit in particular an excellent stomach poison action against insects, but at the same time they have no contact action, or at most only a slight one, even with application of relatively high doses.

The significance of this specific stomach poison action is that compounds of the formula I act only against insects which cause damage, e.g. to plants, by eating, but not against for example the useful insects which live on the plants or which come into contact with the plants.

The compounds of the formula I can be used on their own or together with suitable carriers and/or additives. Suitable carriers and additives may be solid or liquid, and they correspond to the substances common in formulation practice, such as natural or regenerated substances, solvents, dispersing agents, wetting agents, adhesives, thickeners, binders and/or fertilisers.

For application, the compounds of the formula I can be processed into the form of dusts, emulsion concentrates, granulates, dispersions, sprays or solutions, the formulation of these preparations being effected in a manner commonly known in practice.

The agents according to the invention are prepared in a manner known per se by the intimate mixing and-/or grinding of active substances of the formula I with suitable carriers, optionally with the addition of dispersing agents or solvents which are inert to the active substances. The active substances can be obtained and used in the following forms:

solid preparations:
  dusts, scattering agents, granulates (coated granulates, impregnated granulates and homogeneous granulates);
liquid preparations:
  a. water-dispersible active-substance concentrates: wettable powders, pastes or emulsions;
  b. solutions.

The content of active substance in the described agents is between 0.1 and 95%.

The active substances of the formula I can be formulated, for example, as follows:

Dusts:
The following substances are used to produce (a) a 5% dust and (b) a 2% dust:
  a. 5 parts of Active Substance, and
    95 parts of talcum;
  2 parts of Active Substance,
    1 part of highly dispersed silicic acid, and
    97 parts of talcum.

The active substances are mixed and ground with the carriers.

Granulate:
The following substances are used to produce a 5% granulate:
  5 parts of Active Substance,
  0.25 part of epichlorohydrin,
  0.25 part of cetyl polyglycol ether,
  3.50 parts of polyethylene glycol, and
  91 parts of kaolin (particle size 0.3–0.8 mm).

The active substance is mixed with epichlorohydrin and the mixture is dissolved with 6 parts of acetone; the polyethylene glycol and cetyl polyglycol ether are then added. The solution thus obtained is sprayed onto kaolin, and the acetone is subsequently evaporated off in vacuo.

Wettable powders:
The following constituents are used to prepare (a) a 40%, (b) and (c) a 25%, and (d) a 10% wettable powder:
  a. 40 parts of Active Substance,
    5 parts of sodium lignin sulphonate,
    1 part of sodium dibutyl-naphthalene sulphonate, and
    54 parts of silicic acid;
  b. 25 parts of Active Substance,
    4.5 parts of calcium lignin sulphonate,
    1.9 parts of Champagne chalk/hydroxyethyl cellulose, mixture (1:1),
    1.5 parts of sodium dibutyl naphthalene sulphonate,
    19.5 parts of silicic acid,
    19.5 parts of Champagne chalk, and
    28.1 parts of kaolin;
  c. 25 parts of Active Substance,
    2.5 parts of isooctylphenoxy-polyoxyethylene-ethanol,
    1.7 parts of Champagne chalk/hydroxyethyl cellulose mixture (1:1),
    8.3 parts of sodium aluminium silicate,
    16.5 parts of kieselguhr, and
    46 parts of kaolin;
  d. 10 parts of Active Substance,
    3 parts of a mixture of the sodium salts of saturated fatty alcohol sulphates,
    5 parts of naphthalenesulphonic acid/formaldehyde condensate, and
    82 parts of kaolin.

The active substances are intimately mixed, in suitable mixers, with the additives; and the mixture is then ground in the appropriate mills and rollers. Wettable powders are obtained which can be diluted with water to give suspensions of any desired concentration.

Emulsifiable concentrates
The following substances are used to produce (a) a 10%, (b) a 25% and (c) a 50% emulsifiable concentrate:
  a. 10 parts of Active Substance,
    3.4 parts of epoxidised vegetable oil,
    3.4 parts of a combination emulsifier consisting of fatty alcohol polyglycol ether and alkylarylsulphonate calcium salt,
    40 parts of dimethylformamide, and
    43.2 parts of xylene;
  b. 25 parts of Active Substance,
    2.5 parts of epoxidised vegetable oil,
    10 parts of an alkylarylsulphonate/fatty alcohol polyglycol ether mixture,
    5 parts of dimethylformamide, and
    57.5 parts of xylene;
  c. 50 parts of Active Substance,
    4.2 parts of tributylphenol-polyglycol ether,
    5.8 parts of calcium-dodecylbenzenesulphonate,
    20 parts of cyclohexanone, and
    20 parts of xylene.

It is possible to prepare from these concentrates, by dilution with water, emulsions of any desired concentration.

Sprays:
The following constituents are used to produce (a) a 5% spray and (b) a 95% spray:
  a. 5 parts of Active Substance,
    1 part of epichlorohydrin, and
    94 parts of ligroin (boiling limits 160°–190° C); and
  b. 95 parts of Active Substance, and
    5 parts of epichlorohydrin.

EXAMPLE 1

Production of N-(4-chlorophenylsulphonyl)-N'-(3,5-bistrifluoromethylphenyl)-S-methyl-isothiourea Production of the starting material:
  A. N-(4-Chlorophenylsulphonyl)-iminodithiocarbonic acid-S,S-dimethyl ester:

800 g of 50% NaOH (10 moles) and 380 g of carbon disulphide (5 moles) are added dropwise simultaneously at 15° C, with cooling, to a solution of 957 g of 4-chlorobenzenesulphonamide (5 moles) in 2500 ml of dimethylformamide, and the reaction mixture obtained is stirred for about 2 hours at room temperature. There is then added dropwise at 15° C, with cooling, 1260 g of dimethylsulphate (10 moles), and the mixture is stirred for a further 2 hours at 35°. The resulting solution is stirred into water, whereupon the crude product precipitates out as crystals. After filtration with suction, washing in water and a small amount of methanol and drying in vacuo, the N-(4-chlorophenylsulphonyl)-iminodithiocarbonic acid-S,S-dimethyl ester obtained has a melting point of 88°–91° C.

B. N-(4-Chlorophenylsulphony)-S-methyl-iminothiocarbonic acid chlordie

The N-(4-chlorophenylsulphonyl)-iminodithiocarbonic acid-S,S-dimethyl ester (1000 g) obtained in the manner described is suspended in 1000 ml of dichloromethane, and 290 ml of sulphonyl chloride (3.6 moles) is added dropwise to the suspension, whereupon a yellow solution is obtained with generation of $SO_2$. This solution is heated for about 2 hours at a temperature of 35° C. The solvent as well as the formed methanesulphonyl chloride and unreacted sulphonyl chloride is distilled off in a Rotovap, and the crystallised residue is taken up in hexane. After filtration with suction there is obtained N-(4-chlorophenysulphonyl)-S-methyl-iminothiocarbonic acid chloride: m.p. 86°–89° C.

C. Production of the final product: N-(4chlorophenylsulphonyl)-N'-(3,5-bis-trifluoromethyl-phenyl)-S-methylisothiourea:

655 g of 3,5-bis-trifluoromethylaniline (3.85 moles) and 293 g of triethylamine (2.9 moles) are added dropwise, with cooling, to a suspension of 810 g of N-(4-chlorophenylsulphonyl)-S-methyl-iminothiocarbonic acid chloride in 1000 ml of acetonitrile. The reaction mixture is heated for 2 hours, with stirring, at a temperature of 75° C and, after cooling, is stirred into water. The resulting N-(4-chlorophenylsulphonyl)-N'-(3,5-bis-trifluoromethyl-phenyl)-S-methyl-isothiourea is filtered off under suction and washed in ethanol: melting point after drying in vacuo is 141°–143° C.

The following compounds are obtained in an analogous manner:

I. Compounds of the formula

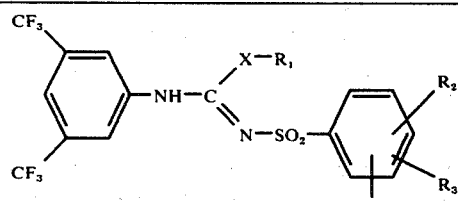

| $R_1$ | $R_2$ | $R_3$ | $R_4$ | X | m.p. |
|---|---|---|---|---|---|
| $CH_3$ | H | 4-$CH_3$ | H | S | 142–144° C |
| $CH_3$ | 2-Cl | 5-Cl | H | S | 181–183° C |
| $CH_3$ | 3-Cl | 4-Cl | H | S | 135–139° C |
| $CH_3$ | 2-Cl | 4-Cl | 5-Cl | S | 213–216° C |
| $CH_3$ | 2-$CH_3$ | H | H | S | 164–166° C |
| n-$C_4H_9$ | H | 4-Cl | H | S | 103–105° C |
| $CH_3$ | H | 4-F | H | S | 153–155° C |
| $CH_3$ | H | 4-$NO_2$ | H | S | 173–178° C |
| $CH_3$ | H | 4-Br | H | S | 110–113° C |
| $CH_3$ | H | 3-Cl | 4-Cl | O | 132–137° C |
| $CH_3$ | 2-Cl | H | 5-Cl | O | 167–169° C |
| $CH_3$ | H | 4-$CH_3$ | H | O | 106–108° C |

II. Compounds of the formula

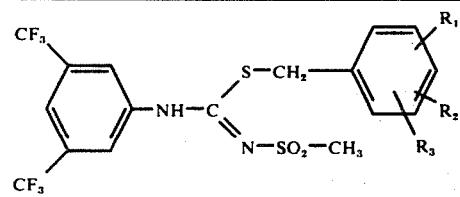

| $R_1$ | $R_2$ | m.p. |
|---|---|---|
| 4-Cl | H | 103–105° C |
| 3-Cl | 4-Cl | 119–121° C |
| 2-Cl | 4-Cl | 127–130° C |
| 2-Cl | 6-Cl | 142–144° C |

-continued

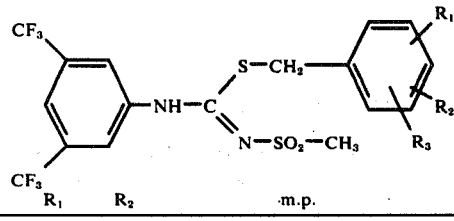

| $R_1$ | $R_2$ | m.p. |
|---|---|---|
| 4-Cl | H | 137–139° C |

III. Compounds of the formulae

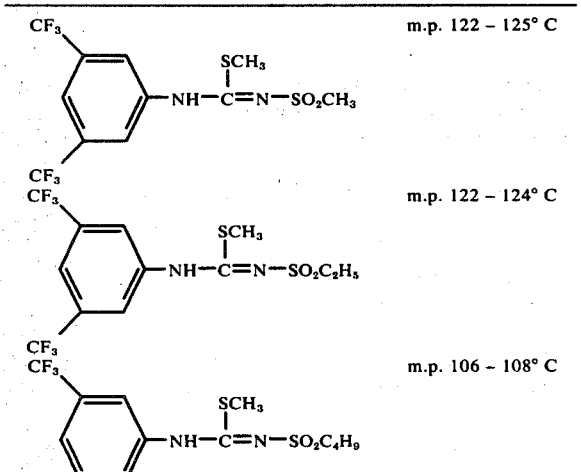

| m.p. |
|---|
| 122 – 125° C |
| 122 – 124° C |
| 106 – 108° C |

EXAMPLE 2

Young mallow plants of the species *Malva silvestris* were completely wetted by immersion in the respective test solutions, and subsequently dried in a greenhouse. The solutions were produced from a 25% wettable powder of the test preparations, and applied at concentrations of 800, 400, 200 and 100 ppm of active substance to the mallow plants.

After drying of the coatings, 1 mallow leaf, which had been protected from premature withering by the placing of a moist cottonwool pad around the petiole, was infested in each case with 5 $L_3$-stages of the test species, namely, *Spodoptera littoralis*, *Heliothis armigera* and *Heliothis virescens*. Plastics Petri dishes were used as containers.

A percentage evaluation of the attained destruction of the larvae was made after 1, 2 and 5 days. If the leaf became completely eaten by the larvae with little insecticidal action, then they received a new leaf from the same treated test plant, and so on until the test was completed. Where, however, there occurred a 100% destruction before reaching the end of the test after 5 days, the identical plant material of the initially treated test plant was infested with 5 new test larvae off the $L_3$-stage. This experimental arrangement thus provided an evaluation of the residual effect of the ageing insecticidal coatings.

The compounds according to Example 1 exhibited in the above test a good stomach-poison action against caterpillars of *Spodoptera littoralis, Heliothis armigera* and *Heliothis virescens*.

EXAMPLE 3

Five young bean plants (*Phaseolus vulgaris*) were treated, in a manner analogous to that in Example 2, by immersion in test solutions of the same dilution series. After drying and infestation with the test insects (*Epilachnea varivestis:* L-4-stage), there was placed over each plant a cellophane bag, which was secured to the pot with a rubber band, and thus prevented the test insects from migrating away from the treated plants. The evaluation was carried out after 2 and 5 days.

The compounds according to Example 1 exhibited in the above test a good stomach-poison action against larvae of *Epilachnea varivestis*.

EXAMPLE 4

The active substance was dissolved in an acetone/water mixture 9:1. In the case of each of 10 test insects (*Spodoptera littoralis* in the L-3 stage), there was applied to the thorax segments 1 ml of the solution containing 0.08 mg of active substances. An evaluation was made after 24 hours.

In this test, the compounds according to Example 1 exhibited no contact action at all, or only the most minute contact action, against larvae of *Spodoptera littoralis*. In comparison to these compounds, the known insecticide, Monocrotophos, caused, with the identical dose, a 100% destruction of the larvae.

EXAMPLE 5

One day before application of the active substance, broad beans (*Vicia faba*) grown in pots were infested with approximately 200 aphides (*Aphis fabae*) per plant. The application was made, by means of a compressed-air sprayer, to the leaves infested with lice, using a spray liquor at a concentration of 1000 ppm (produced from a 25% wettable powder). An evaluation of percentage destruction of the lice was made after 2 and 5 days.

The compounds according to Example 1 had in the above test no action against *Aphis fabae*, whereas the known insecticide, Methylparathion, produced after only 2 days a 100% destruction of the aphides.

We claim:

1. An iso-(thio)-urea derivative of the formula

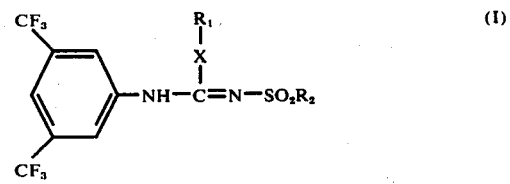

wherein
 $R_1$ and $R_2$ each represent $C_1$–$C_5$-alkyl or phenyl or benzyl mono-, di- or trisubstituted by halogen, trifluoromethyl, nitro methyl, and
 X represents oxygen or sulphur.

2. A compound according to claim 1, wherein $R_1$ represents methyl, $R_2$ represents phenyl mono-, di- or trisubstituted by chlorine, and X represents sulphur.

3. The compound according to claim 2 of the formula

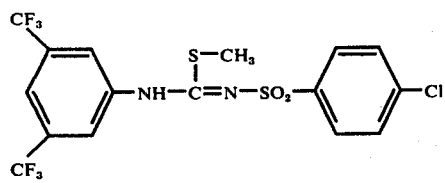

4. The compound according to claim 2 of the formula

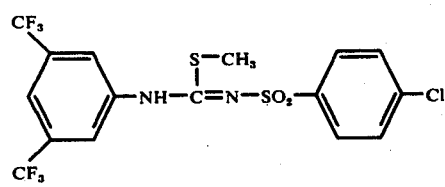

5. An insectidal composition comprising as an active ingredient an insecticidally effective amount of a compound of claim 1 together with a suitable inert carrier.

6. A method for combatting insects which comprises applying to the locus thereof an insecticidally effective amount of a compound of claim 1.

* * * * *

UNITED STATES PATENT AND TRADEMARK OFFICE
CERTIFICATE OF CORRECTION

PATENT NO. : 4,017,638
DATED : April 12, 1977
INVENTOR(S) : Volker Dittrich, et al It is certified that error appears in the above-identified patent and that said Letters Patent are hereby corrected as shown below.

In the Claims:

Change structure in Claim 4 to read as follows:

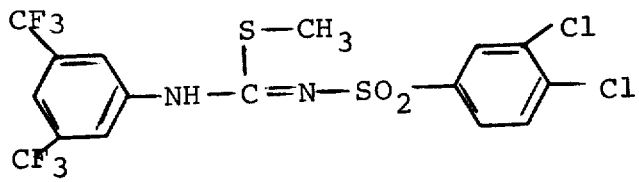

Signed and Sealed this

Twenty-eighth Day of June 1977

[SEAL]

Attest:

RUTH C. MASON
*Attesting Officer*

C. MARSHALL DANN
*Commissioner of Patents and Trademarks*